United States Patent [19]

Cook, Jr. et al.

[11] Patent Number: 5,077,444
[45] Date of Patent: Dec. 31, 1991

[54] PROCESS FOR DRYING HEXABROMOCYCLODODECANE

[75] Inventors: George W. Cook, Jr.; George H. Ransford, both of Magnolia, Ark.

[73] Assignee: Ethyl Corporation, Richmond, Va.

[21] Appl. No.: 614,379

[22] Filed: Nov. 15, 1990

[51] Int. Cl.$^5$ .................... C07C 23/00; C07C 17/02
[52] U.S. Cl. .................... 570/264; 570/246; 570/186; 570/262
[58] Field of Search ............... 570/186, 246, 264, 262

[56] References Cited

U.S. PATENT DOCUMENTS

| | | | |
|---|---|---|---|
| 3,544,641 | 12/1970 | Versnel | 260/648 |
| 3,558,727 | 1/1971 | Jenkner et al. | 260/648 |
| 4,783,563 | 11/1988 | Taniuchi et al. | 570/246 |
| 4,918,253 | 4/1990 | Hermolin et al. | 570/231 |

FOREIGN PATENT DOCUMENTS 3120621 12/1982 Fed. Rep. of Germany .
50-5187 2/1975 Japan .

OTHER PUBLICATIONS

Kirk-Othmer, *Encyclopedia of Chemical Technology*, 2nd Ed., vol. 7, pp. 352-354 (1965).

*Primary Examiner*—Howard T. Mars
*Assistant Examiner*—Kimberly J. Kestler
*Attorney, Agent, or Firm*—David E. LaRose; Richard L. Hansen

[57] ABSTRACT

A flame retardant product predominant in hexabromocyclododecane is prepared and dried by a process wherein gaseous ammonia is injected into the dryer system to prevent the formation of color bodies which contaminant the product.

22 Claims, No Drawings

PROCESS FOR DRYING HEXABROMOCYCLODODECANE

BACKGROUND

This invention relates to a process for drying a product predominant in hexabromocyclododecane such that the formation of color bodies during drying is decreased.

Hexabromocyclododecane (HBCD) is a well known flame retardant agent, suitable for incorporation into various plastics especially polystyrene resins. As with other flame retardant additives, HBCD must fulfill several basic requirements such as melting range, color stability under processing conditions—or, in other words, it must remain colorless in order not to impart an undesired color to the article into which it is incorporated—and it may contain only a restricted amount of contaminants and impurities, such as bromides.

Preparation of HBCD by brominating cyclododecatriene (CDT) has been carried out in a number of different solvents, such as acetic acid, carboxylic acids, halogenated hydrocarbons, lower alcohols and mixtures thereof. The preferred solvent for the preparation of HBCD is a solvent comprising a lower alcohol.

Even when using a lower alcohol solvent, impurities are present in the HBCD product which tend to cause product discoloration. One such impurity is hydrobromic acid (HBr). Another is residual bromine. These impurities may be removed from the product or otherwise neutralized by treating the HBCD product with a basic solution such as $K_2CO_3$, $NaHCO_3$, $CaCO_3$, $NaOH$, $Na_2CO_3$, $NH_4OH$, $NH_4HCO_3$, $(NH_4)_2CO_3$, or gaseous ammonia prior to drying the product. Treatment may be performed before separation, during the separation, or subsequent to the separation of the HBCD product from a reaction mass wherein it is formed. While neutralization of the HBCD reduces the amount undesirable bromides in the dried product, a minor amount of HBr is released during the drying and/or packaging operation. Hydrogen bromide may be released during the drying operation by the decomposition of the moisture laden HBCD and subsequent reaction of the products of the decomposition with the moisture to form HBr and/or HBr which is entrained in the HBCD crystals may be released. When utilizing a dryer containing a significant quantity of ferrous metal, HBr reacts with the iron in the metal to form color bodies comprising iron bromide. These color bodies contribute an undesirable color component to HBCD product which in turn may cause discoloration of thermoplastic formulations using HBCD as a flame retardant. Thus, there is a need for a method to prevent the formation of color bodies in the HBCD product during drying and/or packaging.

THE INVENTION

A process has now been found for drying a product predominant in hexabromocyclododecane (HBCD) in an iron containing dryer system utilizing a gaseous stream to dry the HBCD product, comprising injecting into the gaseous stream an amount of gaseous ammonia sufficient to prevent the formation of color bodies in the HBCD product during drying and/or packaging operations.

The process of this invention allows the use of inexpensive materials in the drying and packaging system for the making an HBCD predominant product without significant discoloration of the product. A particular advantage of this invention is that mild steel can be used for the dryer and/or packaging system thereby decreasing the investment and maintenance costs for the production of the HBCD predominant product. Other advantages of this invention are evident from the ensuing description.

Drying of the HBCD product may be accomplished by contacting the HBCD product with a gaseous stream in an enclosed tubular or rectangular dryer system. The volume of gas in the gaseous stream should be sufficient to dry the particles of HBCD as the particles move through the dryer system. Preferably the gaseous stream not only removes the moisture from the HBCD particles, but also conveys undesirable fine particles and impurities out of the dryer system. The gaseous stream exiting the dryer system can be treated to remove the fines and impurities entrained in the stream prior to recirculation of the stream back to the dryer system.

The gaseous stream which is used should be inert to the HBCD product being dried. Such inert gaseous streams include air, argon, nitrogen, steam, oxygen and the like. Preferably the HBCD predominant product is dried with hot nitrogen.

The amount of flow of the gaseous stream needed to dry the HBCD product is dependent on the moisture content of the HBCD product prior to drying and the dryer system configuration. When the HBCD product has a moisture content of less than about 15% and when using a Wesmont blender-tray dryer system, the flow rate of the gaseous stream may be in a range of from about 100 cubic feet (CF) to about 1500 CF per kilogram of HBCD to be dried. Typically, the hot nitrogen stream used in the dryer is about 400 to about 600 CF per kilogram of HBCD product to be dried.

The temperature of the gaseous stream should be sufficient to remove essentially all of moisture from the HBCD product. The temperature should not be so high that there is a substantial amount of decomposition to the HBCD product as it is dried. Preferably, the temperature of the gaseous stream is less than about 200° C. and most preferably from about 85° to about 130° C. Decomposition of the HBCD product in an atmosphere containing moisture or water may lead to the formation of hydrogen bromide (HBr) which in turn may attack metal components of the dryer system exposed to the HBr. As noted above, when drying HBCD in a dryer system containing iron, a reaction between the HBr and iron forms iron bromides (color bodies) which tend to lessen the desirability of using the HBCD product in flameproofing applications.

To improve the color of an HBCD predominant product and reduce the formation of iron bromides during drying, it has now been found that the injection of an amount gaseous ammonia into the gaseous stream used for drying the HBCD product significantly decreases the amount of color bodies present in the dried HBCD product.

The gaseous ammonia may be injected into the hot gaseous stream before or after contact of the hot gaseous stream with the HBCD particles to be dried. Preferably, the gaseous ammonia is injected into the gaseous stream after heating the gaseous stream to the desired temperature for drying the HBCD. Most preferably the gaseous ammonia is injected after heating the gaseous stream and prior to contact of the gaseous stream with the HBCD product to be dried.

Gaseous ammonia may also be injected in the gaseous stream exiting the dryer to reduce the formation of color bodies in the packaging and dust handling equipment. It has been discovered that there is a detectable amount of HBr which may be released as the product cools after exiting the dryer.

To inject the ammonia into the gaseous stream, it is desirable to utilize a tube inserted through the wall of a duct or conduit carrying the gaseous stream. Preferably, a pitot tube is inserted such that gaseous ammonia is injected into the gaseous stream near the center of the gaseous stream. This provides for thorough mixing of the ammonia with the gaseous stream before the gaseous stream contacts the HBCD product to be dried. Other means known to those skilled in the art may be used for injecting ammonia into the gaseous stream to achieve the purposes of this invention.

The amount of gaseous ammonia needed is dependent on the volume of gas flow in the dryer, the temperature of the hot gaseous stream, and the dryer configuration. Typically from about 0.1 to about 500 standard cubic feet per hour (SCFH) of ammonia is required per 5000 cubic feet per minute (CFM) of total gas flow in the dryer. Preferably a range of from about 1 to about 50SCFH per 5000 CFM of total gas and most preferably from about 3 to about 6 SCFH of ammonia per 5000 CFM of total gas flow is used. More gaseous ammonia may be needed, however, if the dryer configuration is such that quiescent HBCD particles are exposed to hot gas temperatures in excess of about 100° C. for more than about 2 hours. Preferably, the residence time for HBCD particles in a tray-type dryer system ranges from about 1 hour to about 1.5 hours when the initial moisture content of the HBCD particles is less than about 10 wt.%.

In another embodiment, this invention provides a process for the production of a product predominant in 1,2,5,6,9,10-hexabromocyclodecane (HBCD) said process comprising: (a) brominating cyclododecatriene in a solvent comprising isobutanol and from about 2 to about 5 weight percent water; (b) neutralizing the HBCD product with a sodium hydroxide solution; and (c) drying the HBCD product in an iron containing dryer system utilizing a hot gaseous stream, said gaseous stream containing an amount of gaseous ammonia sufficient to prevent the formation of color bodies in the HBCD product during drying.

The product predominant in HBCD may be prepared by a number of well known procedures. One particularly preferred procedure is the bromination of cyclododecatriene in an alcohol solvent containing a molar excess of bromine of from about 1 to about 10 percent in accordance with the general procedure as described in Jenkner et al. U.S. Pat. No. 3,558,727 incorporated herein by reference. Other methods for producing HBCD may be used with the process of this invention as this invention is not limited to the drying of HBCD made by any particular process.

In a particularly preferred embodiment, a product predominant in 1,2,5,6,9,10-hexabromocyclododecane is prepared by brominating cyclododecatriene in an isobutanol solvent containing from about 2 to about 5 weight percent water. At process initiation, the isobutanol solvent containing the desired amount of water is charged to a reaction vessel. The isobutanol may contain less than 2 weight percent water, however, higher yields are obtained when the isobutanol contains at least 2 weight percent water. It is less desirable for the isobutanol to contain more than about 5 weight percent water as a higher water content than about 5 weight percent leads to more difficult separation of the HBCD product from the solvent.

The solvent preferably contains an excess of the stoichiometric amount of bromine required to yield the desired HBCD product. Preferably the solvent contains a molar excess of bromine of from about 2 to about 8 percent.

Once the solvent and excess bromine are in the reaction vessel, a co-feed of cyclododecatriene and bromine is initiated thus forming a reaction mass. The co-feed of cyclododecatriene and bromine is preferably introduced below the liquid surface of the solvent in the reaction vessel. When the co-feed of bromine and cyclododecatriene is complete, the reaction mass is held for a period of time and at a temperature which are sufficient to insure that the reaction is essentially complete.

Subsequent to forming the HBCD product, the product is separated from reaction mass as a wet cake solid. The wet cake containing product is then reslurried in water and the pH is adjusted in a range of from about 5 to 10 and preferably, from about 6 to about 8 with an aqueous NaOH solution. After neutralization, the HBCD product is separated from the aqueous slurry and dried by means of the process of this invention. Separation of the HBCD product from the reaction mass and the aqueous slurry is by conventional techniques such as filtration, centrifugation, decantation and the like.

After separation of the HBCD product from the reaction mass, the reaction mass solvent is neutralized with an aqueous basic solution such as $K_2CO_3$, $NaHCO_3$, $CaCO_3$, NaOH, $Na_2CO_3$, $NH_4OH$, $NH_4HCO_3$, $(NH_4)_2CO_3$ or gaseous ammonia. Preferably an aqueous $Na_2CO_3$ solution is used to neutralize the solvent to a pH of from about 6.8 to about 8.0. When using an aqueous $Na_2CO_3$ solution to neutralize the solvent, two phases are generally formed, a solvent phase and an aqueous phase. After neutralization, the solvent phase is separated from the aqueous phase by decantation. The solvent phase can then be dried by distillation or by stripping the water from the solvent using a stripping medium.

In a particularly preferred embodiment, the solvent phase is heated to form a vapor containing water and isobutanol. This vapor is condensed and collected in a spatially separated vessel as a condensed organic phase and an aqueous phase. Continued heating of the solvent phase provides an essentially dry isobutanol vapor as a stripping medium which is then contacted with the condensed organic phase in a countercurrent stripping operation so as to dry the condensed organic phase to the desired degree. This substantially dry organic phase can then be recycled for use in preparing subsequent batches of HBCD product.

The HBCD product which is formed is a mixture of isomers of 1,2,5,6,9,10-hexabromocyclododecane such as the alpha, beta, and gamma isomers with the gamma isomer being predominant. The melting range of the HBCD product is from about 170° C. to about 195° C. and preferably from about 180° to about 190° C.

Accordingly, the physical characteristics of the HBCD product made by the process of this invention were as follows:

TABLE 1

HBCD Powder

| Sample No. | HBCD (Retained on 60 mesh wt. %) Particle Size | APHA Color | LOD | Melting Point Range (°C.) |
|---|---|---|---|---|
| 1 | 55.8 | 25 | 0.25 | 182-192 |
| 2 | 58.1 | 20 | 0.21 | 181-192 |
| 3 | 72.7 | 15 | 0.18 | 184-193 |
| 4 | 61.6 | 30 | 0.24 | 182-193 |
| 5 | 77.6 | 15 | 0.21 | 182-193 |
| 6 | 64.6 | 25 | 0.23 | 183-191 |

TABLE 2

HBCD Granules

| Sample No. | HBCD (Wt. % >35 mesh) Particle Size | APHA Color | LOD | Melting Point Range (°C.) |
|---|---|---|---|---|
| 1 | 1.47 | 20 | 0.21 | 181-193 |
| 2 | 1.10 | 30 | 0.21 | 181-194 |
| 3 | 2.00 | 30 | 0.23 | 184-193 |
| 4 | 1.60 | 30 | 0.16 | 182-195 |
| 5 | 1.70 | 20 | 0.14 | 184-190 |
| 6 | 3.80 | 10 | 0.16 | 183-192 |
| 7 | 2.70 | 25 | 0.20 | 182-192 |

Variations of this invention are within the spirit and scope of the appended claims.

We claim:

1. A process for drying HBCD in an iron containing dryer system utilizing an inert gaseous stream heated to a temperature below 200° C. to dry the HBCD, said process comprising injecting into said gaseous stream an amount of gaseous ammonia sufficient to prevent the formation of color bodies in the HBCD during said drying operation.

2. The process of claim 1 wherein the amount of gaseous ammonia ranges from about 1 to about 50 standard cubic feet per hour per 5000 cubic feet per minute of total gas flow in said dryer system.

3. The process of claim 1 wherein the amount of gaseous ammonia ranges from about 3 to about 6 standard cubic feet per hour per 5000 cubic feet per minute of total gas flow in said dryer system.

4. The process of claim 1 wherein the HBCD is dried at a temperature of from about 85° C. to about 130° C.

5. The process of claim 1 wherein the gaseous ammonia is injected into the gaseous stream before initial contact of the HBCD with the gaseous stream.

6. The process of claim 1 wherein the HBCD product has a moisture content of less than about 0.5 wt. % after drying.

7. The process of claim 1 wherein the gaseous stream flow ranges from about 400 to about 600 cubic feet per kilogram of HBCD to be dried.

8. The process of claim 1 wherein the HBCD has a pH of from about 6 to about 8 prior to drying.

9. The process of claim 1 wherein the gaseous stream consists essentially of nitrogen.

10. The process of claim 1 wherein the HBCD has a particle size ranging from about 44 to about 246 microns.

11. The process of claim 1 wherein the HBCD subsequent to drying has an APHA color of from about 0 to about 40.

12. The process of claim 1 wherein the HBCD is 1,2,5,6,9,10-hexabromocyclododecane.

13. A process for the production of HBCD, said process comprising:
(a) brominating cyclododecatriene in a solvent comprising isobutanol and from about 2 to about 5 weight percent water;
(b) neutralizing said HBCD product with a sodium hydroxide solution;
(c) drying said HBCD in an iron containing system utilizing a nitrogen gas stream heated to a temperature below 200° C., said nitrogen gas stream containing an amount of gaseous ammonia sufficient to prevent the formation of color bodies in the HBCD during said drying.

14. The process of claim 13 wherein the amount of gaseous ammonia ranges from about 1 standard cubic feet per hour to about 50 standard cubic feet per hour per 5000 cubic feet per minute of total gas flow in said dryer.

15. The process of claim 13 wherein the amount of gaseous ammonia ranges from about 3 standard cubic feet per hour to about 6 standard cubic feet per hour per 5000 cubic feet per minute of total gas flow in said dryer.

16. The process of claim 15 wherein the HBCD is dried at a temperature of from about 85 ° C. to about 130 ° C.

17. The process of claim 16 wherein the gaseous ammonia is injected the nitrogen gas stream before initial contact of the HBCD with the nitrogen gas stream.

18. The process of claim 17 wherein the HBCD has a moisture content of less than about 0.5 wt. % after drying.

19. The process of claim 18 wherein the hot nitrogen gas stream flow ranges from about 400 to about 600 cubic feet per kilogram of HBCD to be dried.

20. The process of claim 19 wherein the HBCD has a pH of from about 6 to about 8 prior to drying.

21. The process of claim 20 wherein the HBCD has a particle size ranging from about 44 to about 246 microns.

22. The process of claim 21 wherein the HBCD subsequent to drying has an APHA color of from about 0 to about 40.

* * * * *